US00RE50949E

(19) United States
(12) Reissued Patent
Chadha et al.

(10) Patent Number: US RE50,949 E
(45) Date of Reissued Patent: Jul. 14, 2026

(54) TEXTURED WOVEN FABRIC FOR USE IN IMPLANTABLE BIOPROSTHESES

(71) Applicant: EDWARDS LIFESCIENCES CORPORATION, Irvine, CA (US)

(72) Inventors: Ajay Chadha, Irvine, CA (US); Son V. Nguyen, Irvine, CA (US); Kevin D. Rupp, Irvine, CA (US)

(73) Assignee: Edwards Lifesciences Corporation, Irvine, CA (US)

(21) Appl. No.: 18/198,643

(22) Filed: May 17, 2023

Related U.S. Patent Documents

Reissue of:
(64) Patent No.: 11,008,676
Issued: May 18, 2021
Appl. No.: 15/378,375
Filed: Dec. 14, 2016

U.S. Applications:
(60) Provisional application No. 62/268,363, filed on Dec. 16, 2015.

(51) Int. Cl.
*A61F 2/24* (2006.01)
*D02G 3/36* (2006.01)
(Continued)

(52) U.S. Cl.
CPC ..... *A61F 2/24* (2013.01); *D02G 3/36* (2013.01); *D02G 3/448* (2013.01); *D03D 27/02* (2013.01);
(Continued)

(58) Field of Classification Search
CPC ..... A61F 2/24; A61F 2210/0076; D02G 3/36; D02G 3/448; D03D 27/02; D03D 27/04;
(Continued)

(56) References Cited

U.S. PATENT DOCUMENTS 3,058,290 A * 10/1962 Leslie ..... D03D 15/00 139/426 R
3,763,858 A * 10/1973 Buese ..... A61L 15/12 428/308.4
(Continued)

FOREIGN PATENT DOCUMENTS

CN 102271620 A 12/2011
CN 103590177 2/2014
(Continued)

OTHER PUBLICATIONS

International Search Report and Written Opinion from corresponding International Application No. PCT/US2016/067138, dated Apr. 20, 2017.
(Continued)

*Primary Examiner* — Catherine S Williams
(74) *Attorney, Agent, or Firm* — Meunier Carlin & Curfman LLC

(57) ABSTRACT

A textured fabric for an implantable bioprosthesis is provided. The textured fabric can include a woven base layer and a plurality of loops projecting from the woven base layer. The plurality of loops are formed from a composite core-sheath yarn. The core can be made of a material that is different from the sheath. The core material can be selected to impart strength and resiliency to bending and the sheath material can be selected to impart a larger surface area or texture that facilitates cellular or tissue in-growth.

54 Claims, 5 Drawing Sheets

(51) Int. Cl.

| | |
|---|---|
| ***D02G 3/44*** | (2006.01) |
| ***D03D 27/02*** | (2006.01) |
| ***D03D 27/04*** | (2006.01) |
| ***D03D 27/06*** | (2006.01) |
| *A61L 27/06* | (2006.01) |

(52) U.S. Cl.
CPC ..... *D03D 27/04* (2013.01); *D03D 27/06* (2013.01); *A61F 2210/0076* (2013.01); *A61L 27/06* (2013.01); *A61L 2400/16* (2013.01); *A61L 2430/20* (2013.01); *D10B 2401/046* (2013.01)

(58) Field of Classification Search
CPC ..... D03D 27/06; A61L 27/06; A61L 2400/16; A61L 2430/20; A61L 27/16; A61L 27/18; D10B 2401/046; C08L 23/06; C08L 23/12; C08L 27/18; C08L 77/00
See application file for complete search history.

(56) References Cited

U.S. PATENT DOCUMENTS 3,983,761 A * 10/1976 Stewart ..... A24C 5/1857 198/846
3,988,490 A * 10/1976 Holroyd ..... D03D 15/00 442/187
4,035,849 A 7/1977 Angell et al.
4,047,252 A * 9/1977 Liebig ..... A61L 27/507 66/196
4,078,110 A * 3/1978 Fletcher ..... B29C 70/24 428/913
4,084,622 A * 4/1978 Nakagawa ..... D02G 1/0286 139/420 R
4,191,221 A * 3/1980 Boyer ..... D02G 3/36 139/426 R
4,324,824 A * 4/1982 Narens ..... D03D 27/00 428/92
4,340,091 A * 7/1982 Skelton ..... A61F 2/06 87/8
4,404,703 A * 9/1983 Woodall, Jr. ..... B05C 17/0207 15/230.11
4,404,999 A * 9/1983 Woodall, Jr. ..... D03D 27/00 139/391
4,420,529 A * 12/1983 Westhead ..... D03D 15/0005 139/383 A
4,467,839 A * 8/1984 Westhead ..... D02G 3/402 139/383 A
4,662,886 A * 5/1987 Moorse ..... A61B 17/06166 606/230
4,739,635 A * 4/1988 Conley ..... D04B 21/02 66/190
4,892,539 A * 1/1990 Koch ..... A61F 2/06 623/1.52
5,024,851 A * 6/1991 Goad ..... D03D 15/00 427/2.3
5,047,285 A * 9/1991 Ward ..... D06M 7/00 442/185
5,114,788 A * 5/1992 Nakagawa ..... D06M 15/17 428/304.4
5,119,643 A * 6/1992 Conley ..... D04B 21/02 66/190
5,178,630 A * 1/1993 Schmitt ..... A61F 2/06 623/1.33
5,215,816 A * 6/1993 Shibata ..... D03D 15/00 442/81
5,232,759 A * 8/1993 Golze ..... E02B 3/125 428/89
5,236,447 A * 8/1993 Kubo ..... A61L 27/14 623/1.13
5,244,718 A * 9/1993 Taylor ..... A61F 13/00017 139/420 A
5,282,846 A * 2/1994 Schmitt ..... A61F 2/06 600/36
5,282,848 A * 2/1994 Schmitt ..... D03D 27/00 623/1.33
5,376,118 A * 12/1994 Kaplan ..... A61F 2/08 606/228
5,411,552 A 5/1995 Andersen et al.
5,424,117 A * 6/1995 Heiman ..... A61F 13/00008 128/846
5,545,212 A * 8/1996 Wakabayashi ..... A61L 27/26 623/1.49
5,554,185 A 9/1996 Block et al.
5,635,298 A * 6/1997 Delker ..... D01F 8/14 428/374
5,806,155 A * 9/1998 Malaney ..... D04H 18/04 28/104
5,840,081 A 11/1998 Andersen et al.
6,168,614 B1 1/2001 Andersen et al.
6,202,264 B1 * 3/2001 Ishihara ..... A44B 18/0034 24/442
6,346,492 B1 * 2/2002 Koyfman ..... A61F 2/26 439/416
6,458,153 B1 10/2002 Bailey et al.
6,582,462 B1 6/2003 Andersen et al.
6,652,578 B2 11/2003 Bailey et al.
6,689,162 B1 2/2004 Thompson
6,783,554 B2 * 8/2004 Amara ..... A61B 17/12168 606/151
7,018,408 B2 3/2006 Bailey et al.
7,083,644 B1 * 8/2006 Moroni ..... A61L 27/18 623/1.51
7,618,446 B2 11/2009 Andersen et al.
7,785,366 B2 8/2010 Maurer et al.
7,820,565 B2 * 10/2010 van Heerden ..... D03D 25/005 442/134
7,964,206 B2 * 6/2011 Suokas ..... D04C 1/06 424/422
8,449,606 B2 5/2013 Eliasen et al.
8,726,479 B2 * 5/2014 Kufferath-Kassner ..... D03D 3/08 139/383 R
8,940,041 B2 1/2015 Carlson et al.
9,216,100 B2 * 12/2015 Seibold ..... D03D 27/00
9,393,110 B2 7/2016 Levi et al.
10,221,506 B2 * 3/2019 Yenici ..... D03D 15/04
10,472,744 B2 * 11/2019 Agarwal ..... D03D 13/008
10,562,484 B2 * 2/2020 Helvoort ..... D03D 11/02
10,683,593 B2 * 6/2020 Gupta ..... D03D 15/0033
10,724,165 B2 * 7/2020 Tsiarkezos ..... D06C 23/04
2001/0056303 A1 * 12/2001 Caneiro ..... A61F 2/0063 623/23.76
2002/0116070 A1 * 8/2002 Amara ..... D04B 1/02 623/23.74
2002/0151958 A1 10/2002 Chuter
2003/0190853 A1 * 10/2003 Lovingood ..... D06P 3/8233 442/209
2004/0097148 A1 * 5/2004 Tucker, Jr. ..... D03D 11/02 442/205
2004/0186589 A1 9/2004 Bentele et al.
2004/0215320 A1 10/2004 Machek
2005/0031828 A1 * 2/2005 Yoshida ..... B08B 1/006 428/92
2005/0081341 A1 * 4/2005 McDougall ..... A44B 18/0034 24/445
2005/0096736 A1 5/2005 Osse et al.
2005/0124245 A1 * 6/2005 Liao ..... D02G 3/328 442/197
2005/0203614 A1 9/2005 Forster et al.
2005/0203617 A1 9/2005 Forster et al.
2005/0288775 A1 * 12/2005 Dong ..... D02G 3/12 623/23.74
2006/0009835 A1 * 1/2006 Osborne ..... A16F 2/07 623/1.13
2006/0025857 A1 2/2006 Bergheim et al.
2006/0089672 A1 4/2006 Martinek
2006/0128243 A1 * 6/2006 Kong ..... A41D 31/00 442/182

(56) References Cited

U.S. PATENT DOCUMENTS

2007/0071941 A1* 3/2007 Eleazer ..... B29C 70/24 428/92
2007/0203575 A1 8/2007 Forster et al.
2007/0265700 A1 11/2007 Eliasen et al.
2008/0125853 A1 5/2008 Bailey et al.
2008/0230140 A1* 9/2008 Santens ..... D03D 15/00 139/396
2008/0300602 A1* 12/2008 Schmitt ..... A41B 17/8816 606/93
2009/0171440 A1* 7/2009 Carlson ..... A61F 2/06 623/1.15
2009/0191777 A1* 7/2009 Liao ..... D03D 15/0027 442/184
2009/0218002 A1* 9/2009 Kashihara ..... D03D 1/0035 139/433
2012/0096690 A1* 4/2012 Chou ..... D03D 15/0061 24/445
2012/0116492 A1* 5/2012 Seibold ..... A61F 2/07 623/1.11
2012/0165918 A1* 6/2012 Du ..... D03D 3/06 623/1.15
2012/0171917 A1* 7/2012 Rasmussen ..... D03D 15/00 442/199
2012/0290082 A1* 11/2012 Quint ..... A61F 2/2412 623/2.19
2013/0273795 A1 10/2013 Richter
2015/0127088 A1 5/2015 Carlson et al.
2015/0190552 A1 7/2015 Richter
2015/0203995 A1* 7/2015 Adams ..... D03D 15/12 2/455
2015/0230953 A1 8/2015 Bar et al.
2015/0320556 A1* 11/2015 Levi ..... A61F 2/2427 623/2.11
2015/0354101 A1* 12/2015 Liao ..... D02G 3/324 442/182
2016/0058524 A1* 3/2016 Tehrani ..... A61F 2/07 623/1.34
2017/0088979 A1* 3/2017 Goenka ..... D02G 3/04
2017/0088985 A1* 3/2017 Goenka ..... A47G 9/0253
2018/0103783 A1* 4/2018 Danaher ..... D03D 13/004
2018/0168804 A1* 6/2018 Nguyen ..... A61F 2/2409
2018/0340273 A1* 11/2018 Goenka ..... D02J 1/12
2018/0347078 A1* 12/2018 Goenka ..... D02G 3/04
2019/0134271 A1* 5/2019 Seo ..... A61L 27/3804
2019/0159882 A1* 5/2019 Perkins ..... D03D 1/00
2019/0223868 A1* 7/2019 Coffey ..... D07B 1/025

FOREIGN PATENT DOCUMENTS

CN 103590177 A 2/2014
CN 104786564 A 7/2015
DE 19532846 A1 3/1997
DE 19907646 A1 8/2000
EP 0108171 A1 5/1984
EP 0592410 B1 10/1995
JP 11-244010 9/1999
WO 1991017720 A1 11/1991
WO 01/49213 A2 7/2001
WO 2002028314 A2 4/2002
WO 02/47575 A2 6/2002
WO 2005084595 A1 9/2005
WO 2005102015 A2 11/2005
WO 2006005015 A2 1/2006
WO 2007067942 A1 6/2007
WO WO-2008156826 A2 * 12/2008 ..... A61F 2/07
WO 2010121076 A2 10/2010
WO 2010139340 A1 12/2010

OTHER PUBLICATIONS

European Search Report issued for Application No. 24191685 dated Jan. 31, 2025.

Notice of Opposition and consolidated documents for EP4177388, dated Apr. 15, 2025.

* cited by examiner

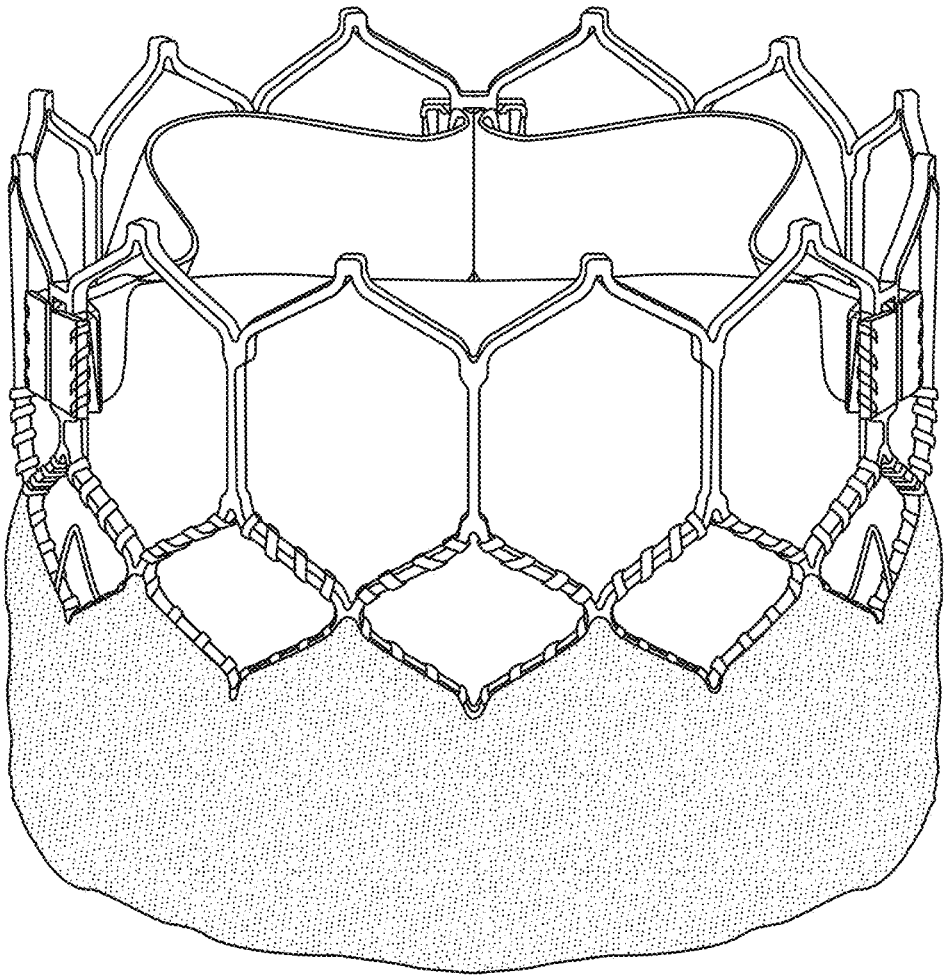
FIG. 5
New

TEXTURED WOVEN FABRIC FOR USE IN IMPLANTABLE BIOPROSTHESES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

*Notice: More than one reissue application has been filed for the reissue of U.S. Pat. No. 11,008,676. The reissue applications are the present application and U.S. application Ser. No. 19/677,253, filed May 14, 2026. This is an application for the reissue of U.S. application Ser. No. 15/378,375, now U.S. Pat. No. 11,008,676, titled "Textured Woven Fabric For Use In Implantable Bioprostheses."* This application claims the benefit of priority under 35 U.S.C. § 119(e) to U.S. Provisional Patent Application Ser. No. 62/268,363, filed on Dec. 16, 2015, the entire contents of which are incorporated by reference as if fully set forth herein.

FIELD OF THE INVENTION

This invention relates to a woven fabric suitable for use in implantable medical devices and, more particularly, to a textured woven fabric suitable for use for in implantable bioprosthetic heart valves.

BACKGROUND

Implantable medical devices often incorporate textiles and fabrics that can fulfill a variety of different functions, depending on the nature and type of the medical device and the site of implantation in a patient.

Implantable bioprosthetic heart valves and stent grafts, for example, often include a layer of fabric, such as an outer covering or inner or outer fabric skirt, which is attached to a metal frame or stent. In the case of bioprosthetic heart valves, the fabric skirt can be used to anchor the valve leaflets to the stent. The fabric skirt can also function to protect the delicate valve leaflets from damage that may otherwise occur from direct contact between the valve leaflets and the stent when the heart valve is radially compressed for delivery through a patient's vasculature.

Cellular and tissue in-growth may be desired for certain implantable medical devices. One reason for this is that it may prevent the implantable medical device from becoming dislodged from the site of implantation. Another reason, particularly with respect to bioprosthetic heart valves, is that it may help prevent the occurrence of paravalvular leakage (PVL), which occurs when blood flows through a space between the implanted bioprosthetic heart valve and the adjacent tissue.

BRIEF SUMMARY

The textured fabrics described herein provide a three-dimensional cloth that can be used in connection with implantable medical devices. The textured fabric can be used as, for example, a skirt that surrounds at least a periphery of an implantable bioprosthetic heart valve.

The textured fabrics can comprise two discrete layers: a base layer and a loop layer. The base layer can be woven and can provide permeability and suture retention strength, as desired. The loop layer can comprise a composite core-sheath yarn, with a core that can be resistant to bending such that it can fill gaps that may exist between, for example, an implanted bioprosthetic heart valve and surrounding tissue. The core yarn can therefore provide improved sealing to mitigate the occurrence of PVL. At the same time, the sheath yarn can be made from a material that is softer than the core yarn to protect the tissue from damage that may otherwise result. The sheath yarn can also be a textured or multifilament yarn that permits cellular and tissue in-growth with the surrounding tissue.

In one embodiment in which the textured fabric is provided to cover a portion of an implantable bioprosthetic heart valve, the composite core-sheath yarns that are used to make up the plurality of loops can provide improved sealing with the surrounding tissue and improved suture retention. These improvements are due to combination of the core yarn's relative strength and resistance to bending, which permits plurality of loops to fill a volume of space or gaps that may exist between the implanted bioprosthetic heart valve and the surrounding tissue. At the same time, the sheath yarns can provide a soft, textured surface that, in combination with the core yarns, not only assists in filling the volume of space or gaps, but also prevents damage to the surrounding tissue.

In one embodiment, a textured fabric for a bioprosthesis is provided. The textured fabric comprises a base layer and a plurality of loops projecting from the base layer. The plurality of loops can be formed from a composite core-sheath yarn. The composite core-sheath yarn can comprise a core and a sheath, wherein the sheath is made from a material different from the core.

In a separate optional aspect, the base layer can be a woven base layer comprising warp and weft yarns.

In another separate optional aspect, the warp and weft yarns can be made from a material each independently selected from the group consisting of: polyester, polyethylene, ultra-high molecular-weight polyethylene ("UHMWPE"), polypropylene, polytetrafluoroethylene ("PTFE"), expanded PTFE ("ePTFE"), and nylon.

In another separate optional aspect, the warp and weft yarns can be made of the same material.

In another separate optional aspect, the warp and weft yarns can be made of different materials.

In another separate optional aspect, the warp and weft yarns of the base layer can have a diameter of about 20 microns to about 70 microns.

In another separate optional aspect, the base layer can have an ends per inch or EPI of about 150 to about 300.

In another separate optional aspect, the base layer can have a picks per inch or PPI of about 100 to about 250.

In another separate optional aspect, the composite core-sheath yarn can comprise a core that is made from a monofilament yarn or a shape memory material.

In another separate optional aspect, the core can be made from a shape memory material and the shape memory material can be an alloy of nickel and titanium.

In another separate optional aspect, the core can be a monofilament yarn selected from the group consisting of: polyester, polyethylene, UHMWPE, polypropylene, PTFE, ePTFE, and nylon.

In another separate optional aspect, the sheath can be made of a textured multifilament yarn.

In another separate optional aspect, the sheath can have a denier of from about 15 to about 40.

In another separate optional aspect, the sheath can have a filament count of from about 5 to about 20.

In another separate optional aspect, the sheath can have a diameter of about 25 microns to about 250 microns.

In another separate optional aspect, the textured fabric can have a loop density of about 400 loops/in$^2$ to about 1,000 loops/in$^2$.

In another separate optional aspect, the loop height can be about 0.0250 inches to about 0.1000 inches.

In another separate optional aspect, the core-sheath yarn can have a twists per inch or TPI of about 20 to about 40.

In another separate optional aspect, the sheath can be wrapped around a core with the sheath being provided externally of the core.

In another separate optional aspect, the core is not wrapped around the sheath.

In another separate optional aspect, a bioprosthetic heart valve is provided that comprises the textured fabric in accordance with any one or a combination of the separate optional aspects described above.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Preferred and non-limiting embodiments of the inventions may be more readily understood by referring to the accompanying drawings in which:

*FIG. 5 is a perspective view of a bioprosthetic heart valve comprising the textured fabric.*

Like numerals refer to like parts throughout the several views of the drawings.

DETAILED DESCRIPTION OF THE EXEMPLARY EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Figure 3:
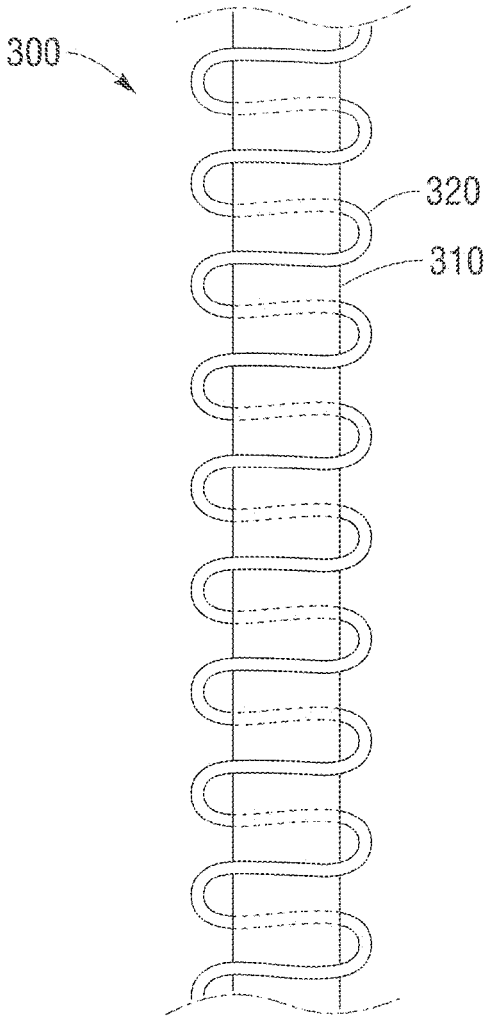
FIG. 3 is a schematic representation of a composite core-sheath yarn that can be used for the loop layer.

Described herein are textured fabrics comprising a woven base layer made from one or a combination of different yarns for the warp and weft yarns and a plurality of loops interlaced with the weft yarn. The warp and weft yarns can be made from the same or from different materials and the loops can be made of a composite yarn that is formed by spiral wrapping a core yarn with a sheath yarn. In one embodiment, only the sheath yarn comprises spiral turns around a core yarn, as depicted in FIG. 3. In another embodiment, both core and sheath yarns comprise spiral turns around one another. The core yarn can be made of a material that is more resistant to bending than the sheath yarn so as to provide resiliency of the formed loops. The sheath yarn can be made from a softer yarn that can help prevent tissue damage that may otherwise occur. The sheath yarn can also be a textured or multifilament yarn to provide an increased surface area to promote cellular attachment and in-growth.

As used herein, "yarns" are understood to comprise one or more filaments and thus include monofilament yarns, multifilament yarns and composite yarns comprising any combination of monofilament and/or multifilament yarns, such as composite core-sheath yarns.

Figure 1:
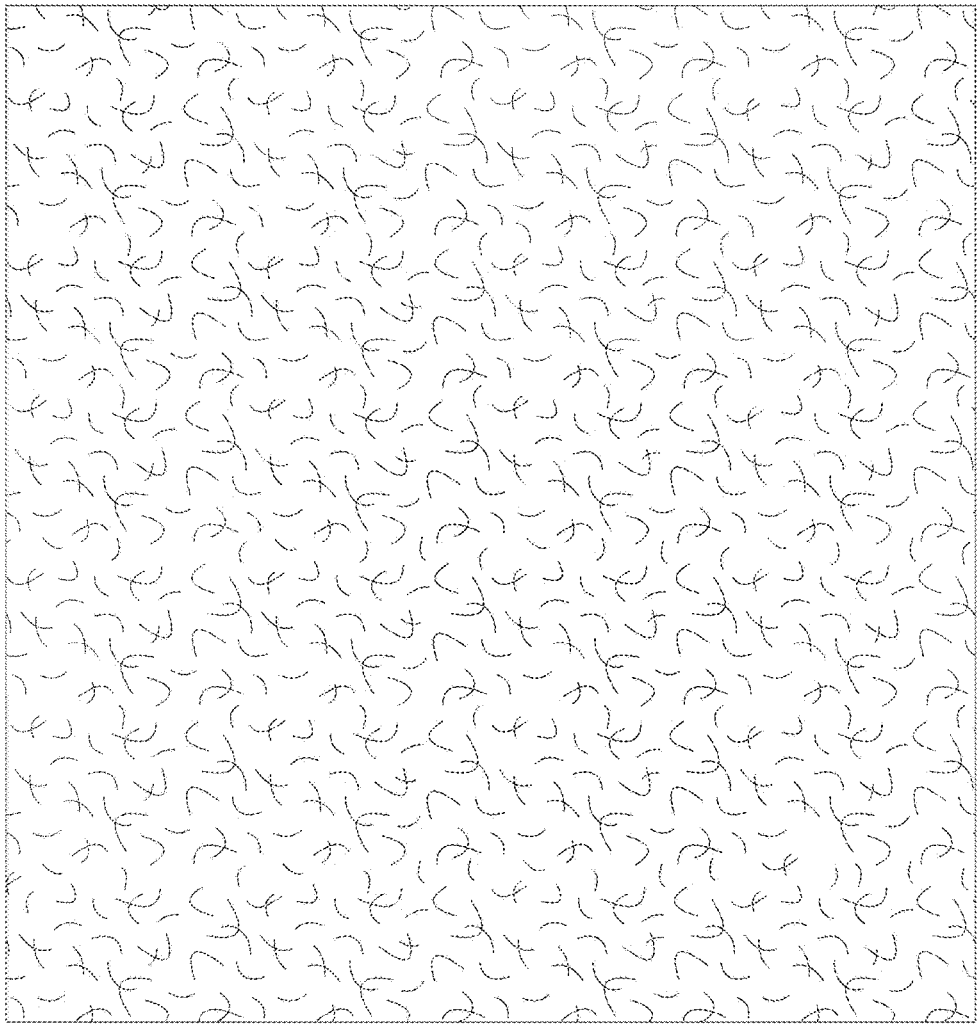
FIG. 1 is a plan view of a textured fabric having a woven base layer and a loop layer in accordance with one embodiment.

FIG. 1 depicts an exemplary embodiment of a textured fabric comprising a woven base layer and a plurality of loops disposed on or extending away from the woven base layer. The woven base layer can comprise one or a combination of yarns. The yarns used in the woven base layer can be a monofilament yarn made from polyester, polyethylene, ultra-high molecular-weight polyethylene ("UHMWPE"), polypropylene, polytetrafluoroethylene ("PTFE"), expanded PTFE yarn ("ePTFE"), or nylon. Alternatively, the yarn can be a multifilament yarn made from one or more of a polyester, polyethylene, polypropylene, PTFE, expanded PTFE yarn, and nylon. In another embodiment, the multifilament yarn can include other synthetic fibers or natural fibers, such as cotton or silk.

The woven base layer can be configured to have any one or more of the following characteristics, depending on the application of the textured fabric: (1) a relatively low thickness or profile; (2) resistance to stretching or shrinking; and (3) permeability to fluids and, more particularly, to bodily fluids such as blood.

The woven base layer is understood to be distinguishable from knitted fabrics in that the woven base layer is constructed by interlacing or weaving lengthwise and crosswise at least two yarns, called warp and weft yarns, to create the woven base layer. In certain embodiments, the woven base layer does not have a great degree of stretchability due to the nature of its construction of interlaced warp and weft yarn. Of course, selection of stretchable yarns in the construction of the woven base layer can impart stretchability of the resulting woven base layer. This is in contrast to a knitted fabric, which is made from interlocking loops that impart a greater degree of stretchability to the resulting knitted fabric, regardless of whether or not the yarns themselves are stretchable.

Thus, in one embodiment, the warp and weft yarns of the woven base layer can be made from yarns that do not stretch to a significant degree, for example, less than about 25%, less than about 20%, less than about 15%, less than about 10%, less than about 5%, or less than about 1%.

In one aspect, the warp and weft yarns of the woven base layer can be made of the same yarn. In another aspect, the warp and weft yarns can each be made of a plurality of different yarns. In a further aspect, the warp and weft can be made from different yarns.

The thickness or profile of the woven base layer can be selected by using warp and weft yarns of a pre-selected diameter, a pre-selected denier, a pre-selected filament count, or any combination of the foregoing depending on the type of yarns used.

In one embodiment, the warp and weft yarns of the woven base layer can each independently have a diameter of about 10 microns, about 15 microns, about 20 microns, about 25 microns, about 30 microns, about 35 microns, about 40 microns, about 45 microns, about 50 microns, about 55 microns, about 60 microns, about 65 microns, about 70 microns, about 75 microns, or about 80 microns. In a preferred embodiment, the diameters of the warp and weft yarns of woven base layer can separately be provided within a range between and including any two of the foregoing values. For example, the diameters of the warp and weft yarns of the woven base layer can be provided in the range of about 20 microns to about 70 microns.

In another embodiment, the warp or weft yarns of the woven base layer can each independently have a denier of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 71, 73, 74, 75, 76, 77, 78, 79, 80, 81, 82, 83, 84, 85, 86, 87, 88, 89, 90, 91, 92, 93, 94, 95, 96, 97, 98, 99, or 100. In a preferred embodiment, the denier for warp or weft yarns of the woven base layer can separately be provided within a range between and including any two of the foregoing values. For example, the denier for the warp or weft yarns of the woven base layer yarn can be provided in the range of about 7 denier to about 70 denier.

In a further embodiment, the warp and weft yarns of the woven base layer can each independently have a filament count of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60. In a preferred embodiment, the filament count for each of the warp and weft yarns can independently be provided within a range between and including any two of the foregoing values. For example, the filament count can be provided in a range of about 5 to about 40 filaments.

The permeability of the woven base layer can be adjusted by varying the pore sizes of the woven base layer as defined by adjacent warp and weft yarns. This can be accomplished by the selection of the yarns and/or by varying the ends per inch and the picks per inch of the woven base layer.

In one embodiment, the ends per inch (EPI) for the woven base layer can be about 100 EPI, 105 EPI, 110 EPI, 115 EPI, 120 EPI, 125 EPI, 130 EPI, 135 EPI, 140 EPI, 145 EPI, 150 EPI, 155 EPI, 160 EPI, 165 EPI, 170 EPI, 175 EPI, 180 EPI, 185 EPI, 190 EPI, 195 EPI, 200 EPI, 205 EPI, 210 EPI, 215 EPI, 220 EPI, 225 EPI, 230 EPI, 235 EPI, 240 EPI, 245 EPI, 250 EPI, 255 EPI, 260 EPI, 265 EPI, 270 EPI, 275 EPI, 280 EPI, 285 EPI, 290 EPI, 295 EPI, 300 EPI, 305 EPI, 310 EPI, 315 EPI, 320 EPI, 325 EPI, 330 EPI, 335 EPI, 340 EPI, 345 EPI, or 350 EPI. In a preferred embodiment, the EPI can be provided within a range between and including any two of the foregoing values. For example, the EPI can be provided in the range of about 150 to about 300 EPI.

In another embodiment, the picks per inch (PPI) for the woven base layer can be about 50 PPI, 55 PPI, 60 PPI, 65 PPI, 70 PPI, 75 PPI, 80 PPI, 85 PPI, 90 PPI, 95 PPI, 100 PPI, 105 PPI, 110 PPI, 115 PPI, 120 PPI, 125 PPI, 130 PPI, 135 PPI, 140 PPI, 145 PPI, 150 PPI, 155 PPI, 160 PPI, 165 PPI, 170 PPI, 175 PPI, 180 PPI, 185 PPI, 190 PPI, 195 PPI, 200 PPI, 205 PPI, 210 PPI, 215 PPI, 220 PPI, 225 PPI, 230 PPI, 235 PPI, 240 PPI, 245 PPI, 250 PPI, 255 PPI, 260 PPI, 265 PPI, 270 PPI, 275 PPI, 280 PPI, 285 PPI, 290 PPI, 295 PPI, or 300 PPI. In a preferred embodiment, the PPI can be provided within a range between and including any two of the foregoing values. For example, the PPI can be provided in the range of about 100 to about 250 PPI.

Figure 2A:
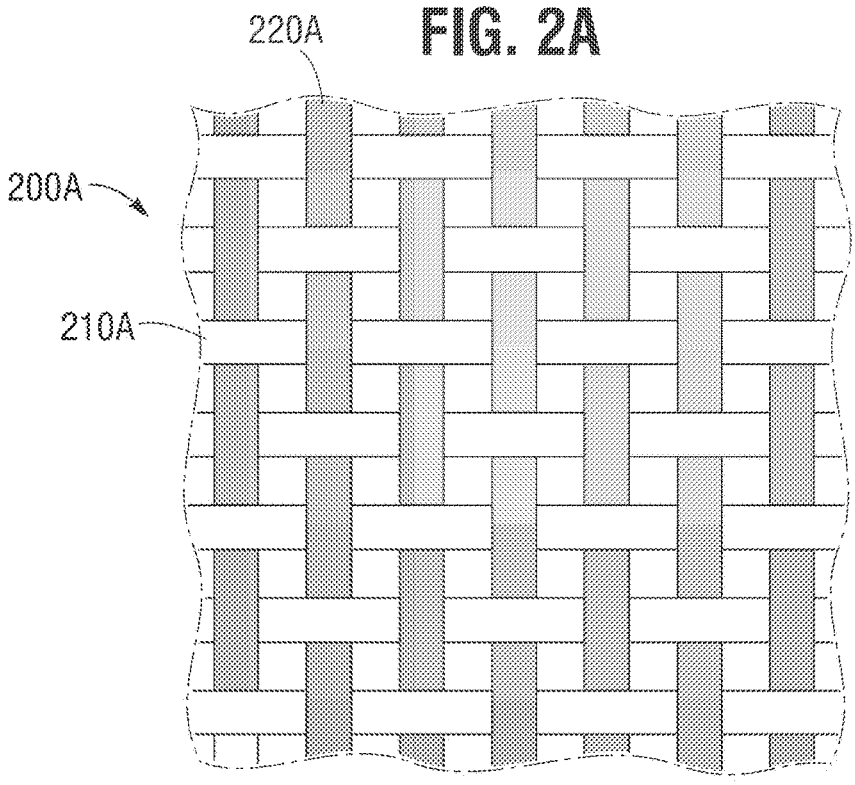
FIGS. 2A and 2B are schematic representations of weave patterns for the woven base layer.
Figure 2B:
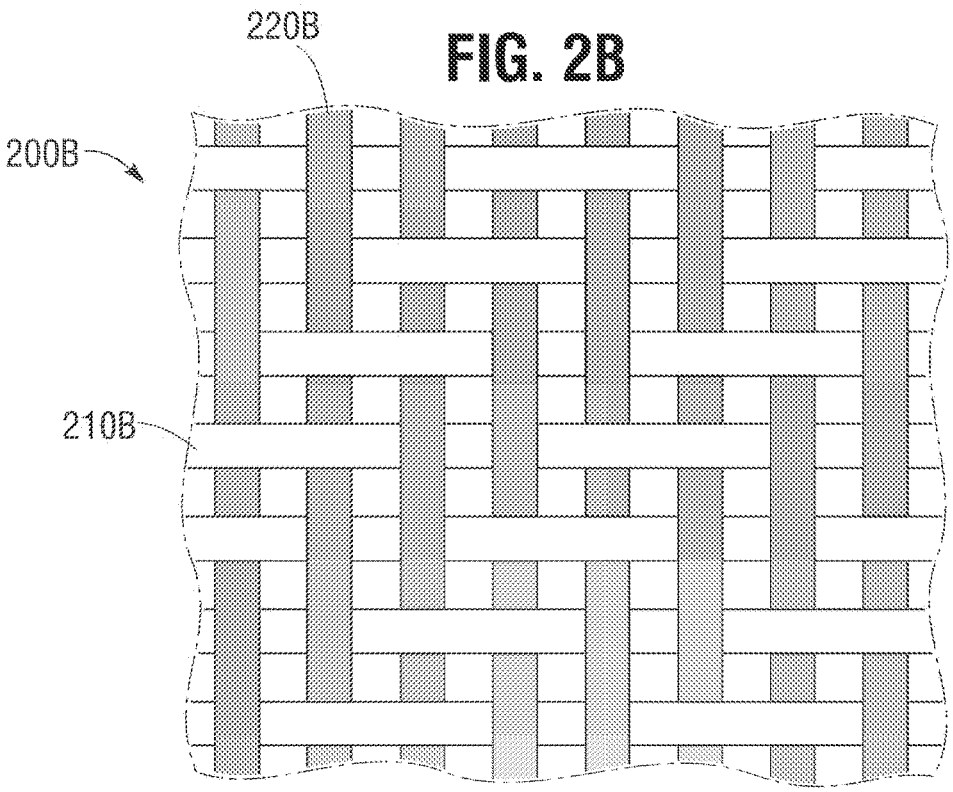

The permeability of the woven base layer can also be adjusted by selecting a specific weave pattern. The weave pattern for the woven base layer can be plain, twill or satin. FIGS. 2A and 2B depict exemplary embodiments of the woven base layer. In both embodiments, the woven base layer is depicted as comprising warp and weft yarns. FIG. 2A depicts a plain weave, in which each weft yarn goes alternately over and under a warp yarn and each warp yarn goes alternately over and under each weft yarn. FIG. 2B depicts a twill weave, in which each weft yarn is passed over two warp yarns with a step or offset between rows of weft yarns to create the diagonal pattern that is characteristic of twill weaves.

A plurality of loops can be provided in conjunction with the woven base layer to provide a textured surface that facilitates cellular and tissue in-growth. The plurality of loops can also fill a volume of space between a bioprosthesis and an adjacent tissue at the site of implantation. This may be particularly desirable for bioprosthetic heart valves and, in particular, for the prevention of PVL that can result from inadequate sealing between the implant and the surrounding tissue. The plurality of loops can be provided to fill an open volume or space between the bioprosthetic heart valve and the tissue at the site of implantation to facilitate cellular and tissue in-growth and also to prevent or block the occurrence of PVLs.

The height of the individual loops and the loop density provided on the woven base layer can be adjusted based on the desired volume that is sought to be filled at the implantation site.

The plurality of loops can each have a loop height of about 0.0200 inches, 0.0250 inches, 0.0300 inches, 0.0350 inches, 0.0400 inches, 0.0450 inches, 0.0500 inches, 0.0550 inches, 0.0600 inches, 0.0650 inches, 0.0700 inches, 0.0750 inches, 0.0800 inches, 0.0850 inches, 0.0900 inches, 0.0950 inches, 0.1000 inches, 0.1050 inches, or 0.1100 inches. In a preferred embodiment, the loop height can be provided within a range between and including any two of the foregoing values. For example, the loop height can be provided in the range of from about 0.0250 inches to about 0.1000 inches.

The plurality of loops can have a loop density of about 300 loops/in$^2$, 350 loops/in$^2$, 400 loops/in$^2$, 450 loops/in$^2$, 500 loops/in$^2$, 550 loops/in$^2$, 600 loops/in$^2$, 650 loops/in$^2$, 700 loops/in$^2$, 750 loops/in$^2$, 800 loops/in$^2$, 850 loops/in$^2$, 900 loops/in$^2$, 950 loops/in$^2$, 1,000 loops/in$^2$, 1,050 loops/in$^2$, 1,100 loops/in$^2$, 1,150 loops/in$^2$, or 1,200 loops/in$^2$. In a preferred embodiment, the loop density can be provided within a range between and including any two of the foregoing values. For example, the loop density can be provided in the range from about 400 loops/in$^2$ to about 1,000 loops/in$^2$.

Each of the plurality of loops can be formed from composite core-sheath yarns. The composite core-sheath yarns can be comprised of at least two different types of materials. The core can be made of a material such that the formed loop is compressible and returns to its loop shape when compression is released. The core can be made of a resilient material that is more resistant to bending than the sheath material. The sheath material can be made of a textured material with a relatively softer and larger surface area than the core. The softer material of the sheath can help protect the tissue from damage that may otherwise result. The textured surface of the sheath can facilitate cellular infiltration and in-growth.

In one embodiment in which the textured fabric is provided to cover a portion of an implantable bioprosthetic heart valve, the composite core-sheath yarns that are used to make up the plurality of loops can provide improved sealing with the surrounding tissue and improved suture retention. These improvements are due to combination of the core yarn's relative strength and resistance to bending, which permits plurality of loops to fill a volume of space or gaps that may exist between the implanted bioprosthetic heart valve and the surrounding tissue. At the same time, the sheath yarns can provide a soft, textured surface that, in combination with the core yarns, not only assists in filling the volume of space or gaps, but also prevents damage to the surrounding tissue.

In one embodiment, the resiliency and the resistance to bending of the core yarn of the core-sheath yarn can result from selecting a material for the core yarn that is more resistant to bending or is stiffer than the sheath yarn. The core yarn can be made of, for example, a monofilament yarn or a shape memory material or alloy, such as a super elastic nitinol. The resiliency and resistance to bending of the core yarn can also be increased by increasing the diameter of the core yarn.

On the other hand, sheath yarn can be selected to provide an outer surface that is soft, textured, has a high surface area, or any combination of the foregoing, so as to promote cellular or tissue in-growth and also to prevent damage to the surrounding tissue. These properties can be enhanced by selecting the appropriate diameter, denier, filament count or any of the foregoing for the sheath yarn. Additionally, the sheath yarn can be provided to have a greater surface area per unit length than the core yarn.

In one embodiment, the diameter of the core material of the core-sheath yarn can depend upon the inherent stiffness of the material selected. The greater the inherent stiffness, the smaller the diameter. The diameter of the core yarn can be about 0.0005 inches, 0.0010 inches, 0.0015 inches, 0.0020 inches, 0.0025 inches, 0.0030 inches, 0.0035 inches, 0.0040 inches, 0.0045 inches, 0.0050 inches, 0.0055 inches, 0.0060 inches, 0.0065 inches, or 0.0070 inches. In one embodiment, the diameter of the core yarn can be less than 0.0005 inches or greater than 0.0070 inches. In another embodiment, the diameter of the core yarn can be provided within a range between and including any two of the foregoing values. For example, the range can be from about 0.0005 inches to about 0.0020 inches. In one embodiment, the diameter of the core yarn can be less than the diameter of the sheath yarn. In another embodiment, the diameter of the core yarn can be greater than the diameter of the sheath yarn.

The sheath material of the core-sheath yarn can be made from a textured yarn, preferably a multifilament yarn. In one embodiment, the textured yarn can have a denier of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In one embodiment the denier can be greater than 50. In another embodiment, the denier can be provided within a range between and including any two of the foregoing values. For example, the denier can be provided in the range of from about 15 to about 40.

The sheath material of the core-sheath yarn can also be made from a textured yarn having a filament count that facilitates cellular or tissue in-growth. In one embodiment, the filament count can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In one embodiment, the filament count can be greater than 50. In another embodiment, the filament count can be provided within a range between and including any two of the foregoing values. For example, the filament count can be provided in the range of about 5 to about 20. The higher the filament count, the greater the surface area to facilitate cellular and tissue in-growth.

The diameter of the sheath material can also be selected. In one embodiment, the diameter of the material, in microns, can be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 80, 90, 100, 110, 120, 130, 140, 150, 160, 170, 180, 190, 200, 210, 220, 230, 240, 250, 260, or 270. Ina further embodiment, the diameter can be greater than 270 microns. In yet a further embodiment, the diameter can be provided within a range between and including any two of the foregoing values. For example, the diameter can be provided within a range of about 25 microns to about 250 microns.

FIG. 3 depicts an embodiment of the core-sheath yarn 300 that can be used for the plurality of loops. As can be seen, the core-sheath yarn comprises a core material 310 and a sheath material 320 that is wrapped around the core material 310. In the embodiment depicted in FIG. 3, the core material 310 is not itself wrapped around the sheath material 320. Rather, it is the sheath material 320 that is spiral wrapped around the core material 310. Thus, the core material 310 generally defines a longitudinal axis around which the sheath material 320 wraps.

The parameters of coil length and coil pitch of the sheath material influences the extent to which the sheath material covers the core material. These parameters can be controlled by the rotational speed of two hollow spindles that are normally used for making the composite core-sheath yarn, the delivery speed of the sheath material and the core stretch ratio during wrapping.

In one embodiment, the sheath material of the core-sheath yarn is characterized as having a twist per inch (TPI) of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60. As used herein, the TPI refers to the number of twists of only the sheath material around the core in a single linear inch along the core length. In one embodiment, the TPI count can be less than 5 or greater than 60. In another embodiment, the TPI can be provided within a range between and including any two of the foregoing values. For example, the TPI can be provided in the range of about 10 to about 25 or about 20 to about 40.

It is understood that the processing parameters for creating a core-sheath yarn having a TPI of a specific value or within a range of values depends on a number of parameters. As previously described, the composite core-sheath yarn is a two-component structure that is produced by, for example, a ring spinning system. Among the parameters that affect the resulting TPI of the composite core-sheath yarn is the core stretch ratio, which is governed by the relative speed of the pre-draft roller and the delivery roller of the ring spinning system. The sheath yarn is spiral wrapped between the portion of the core yarn that extends between, or in some instances, is stretched between the pre-draft and delivery rollers.

In one embodiment, the core stretch ratio is about 1 in which the speed of the pre-draft roller and the delivery roller are the same. In another embodiment, the core stretch ratio is greater than 1, in which the speed of the delivery roller is greater than the speed of the pre-draft roller. In accordance with this embodiment, the core stretch ratio can be about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0. In one embodiment, the core stretch ratio can be greater than 4.0. In another embodiment, the core stretch ratio can be provided within a range between and including any two of the foregoing values. For example, the core stretch ratio can be provided in the range of about 1.5 to about 3.5. In a further embodiment, the core stretch ratio can be provided in the range of about 2.4 to about 2.8.

Figure 4:
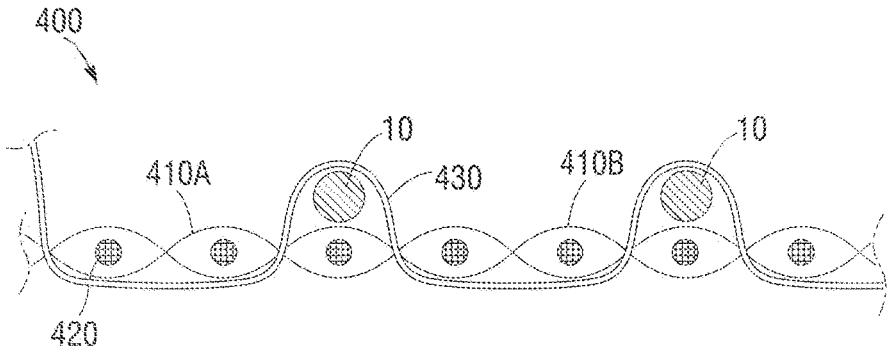
FIG. 4 is a cross-sectional view of an embodiment of the textured fabric.

FIG. 4 is a cross-sectional view of an embodiment of the textured fabric 400 comprising a woven base layer and a plurality of loops. The woven base layer can be formed by interweaving a first set of warp yarns 410A and 410B with a plurality of weft yarns 420. The plurality of loops can be formed by interweaving a second set of warp yarns 430 through one or a plurality of weft yarns 420 and over metal rods or wires 10. In one embodiment, the rods or wires 10 can be provided directly adjacent the woven base layer. In another embodiment, the rods or wires 10 are provided at a pre-determined distance above the woven base layer to provide a loop of greater height. The loop density can be increased by increasing the number of metal rods or wires 10 and decreasing the distance between adjacent metal rods or wires 10.

In one embodiment, the desired loop height and width can be controlled by the diameter of the metal rods or wires 10 that is placed directly adjacent the woven base layer. As depicted in FIG. 4, the metal rods or wires 10 can be provided as a cylinder to provide a resulting loop in which the height is substantially the same as the width. Alternatively, the metal rods or wires can be provided in a different shape, such as an oval shape, to provide a resulting loop in which the height and width are different, depending on the orientation of the oval-shaped metal rods or wires. In one embodiment, one or both of the loop height and width is about 0.0200 inches, 0.0250 inches, 0.0300 inches, 0.0350 inches, 0.0400 inches, 0.0450 inches, 0.0500 inches, 0.0550 inches, 0.0600 inches, 0.0650 inches, 0.0700 inches, 0.0750 inches, 0.0800 inches, 0.0850 inches, 0.0900 inches, 0.0950 inches, 0.1000 inches, 0.1050 inches, or 0.1100 inches. In one aspect, the loop height is greater than the loop width. In another aspect, the loop width is greater than the loop height. In a preferred embodiment, the loop height and/or width can be provided within a range between and including any two of the foregoing values. For example, the loop height can be provided in the range of from about 0.0250 inches to about 0.1000 inches and the loop width can be provided in the range of from about 0.0250 inches to about 0.1000 inches.

The textured woven fabrics described herein can be incorporated in any suitable medical device that is introduced temporarily or permanently into the body for the treatment of a medical condition. Such medical devices can include, but are not limited to, prosthetic heart valves, annuloplasty rings, docking devices such as pre-stents or coils that retain other implanted devices, endovascular grafts, stent grafts, meshes, vascular grafts, tissue scaffolds, myocardial plugs, venous valves, and other known biocompatible devices.

The textured fabrics described herein are particularly suitable for implantable medical devices for which attachment to a biological tissue and cellular and tissue in-growth is desired. For example, the textured fabrics are particularly suitable for bioprosthetic heart valves and various types of vascular stents. In the case of bioprosthetic heart valves, the textured fabrics can be particularly suitable for use as an inner or outer skirt that can cover a frame or a stent. Exemplary heart valves for which the textured woven fabrics can be used are described in U.S. Pub. No. 2012/0123529, published on May 17, 2012, the entire contents of which are incorporated herein by reference in their entirety.

It is to be understood that the detailed description and specific examples, while indicating preferred embodiments of the present disclosure, are given by way of illustration and not limitation. Many changes and modifications within the scope of the present disclosure may be made without departing from the spirit thereof, and the disclosure includes all such modifications.

The invention claimed is:

1. A textured fabric for a bioprosthesis comprising:

a base layer; and a plurality of loops projecting from the base layer;

wherein the plurality of loops is formed from a composite core-sheath yarn; and wherein the base layer is a woven base layer comprising warp and weft yarns and wherein the base layer comprises yarns having a diameter of about 20 microns to about [70 ] *80* microns;

wherein the composite core-sheath yarn comprises a core that is made from a monofilament yarn or a shape memory metal and a sheath that is made from a textured multifilament yarn *having a filament count from 5 filaments to 20 filaments*;

wherein the sheath has a diameter of about [25 ] *10*microns to about 250 microns; and wherein the [textured fabric] *plurality of loops* has a loop density [of about 400 ] *from 900* loops/in$^2$ to [about 1,000 ] *1,200* loops/in$^2$.

2. The textured fabric of claim 1, wherein the warp and weft yarns are made from a material each independently selected from the group consisting of: polyester, polyethylene, ultra-high molecular-weight polyethylene ("UHMWPE"), polypropylene, polytetrafluoroethylene ("PTFE"), expanded PTFE ("ePTFE"), and nylon.

3. The textured fabric of claim 1, wherein the warp and weft yarns are made of the same material.

4. The textured fabric of claim 1, wherein the warp and weft yarns are made of different materials.

5. The textured fabric of claim 1, wherein the base layer has an EPI of about 150 to about 300.

6. The textured fabric of claim 1, wherein the base layer has a PPI of about 100 to about 250.

7. The textured fabric of claim 1, wherein the core is made from the shape memory material and wherein the shape memory material is an alloy of nickel and titanium.

8. The textured fabric of claim 1, wherein the core is the monofilament yarn and wherein the monofilament yarn is selected from the group consisting of: polyester, polyethylene, UHMWPE, polypropylene, PTFE, ePTFE, and nylon.

9. The textured fabric of claim 1, wherein the sheath has a denier of from about 15 to about 40.

[10. The textured fabric of claim 1, wherein the sheath has a filament count of from about 5 to about 20.]

11. The textured fabric of claim 1, wherein the sheath is wrapped around a core, the sheath being provided externally of the core.

12. A bioprosthetic heart valve comprising the textured fabric of claim 1.

13. A textured fabric for a bioprosthesis comprising:

a base layer *comprising yarns having a diameter from 20 microns to 80 microns*; and a plurality of loops projecting from the base layer[,] *the plurality of loops comprising a textured multifilament yarn having a diameter from 10 microns to 250 microns and a filament count from 5 filaments to 20 filaments;*

[wherein the plurality of loops is formed from a composite core-sheath yarn; and]

wherein the [textured fabric] *plurality of loops* has a loop density [of about 400 ] *from 900* loops/in$^2$ to [about 1,000 ] *1,200* loops/in$^2$.

14. The textured fabric of claim 13, wherein the base layer is a woven base layer comprising warp and weft yarns.

15. The textured fabric of claim [14] *13*, wherein the [warp and weft] *base layer comprises* yarns [are] made from a material [each] independently selected from the group consisting of: polyester, polyethylene, ultra-high molecular-weight polyethylene ("UHMWPE"), polypropylene, polytetrafluoroethylene ("PTFE"), expanded PTFE ("ePTFE"), and nylon.

16. The textured fabric of claim 14, wherein the warp and weft yarns are made of the same material.

17. The textured fabric of claim 14, wherein the warp and weft yarns are made of different materials.

[18. The textured fabric of claim 14, wherein the base layer comprises yarns having a diameter of about 20 microns to about 70 microns.]

19. The textured fabric of claim 14, wherein the base layer has an EPI of about 150 to about 300.

20. The textured fabric of claim 14, wherein the base layer has a PPI of about 100 to about 250.

21. The textured fabric of claim 13, *wherein the plurality of loops is formed from a composite core-sheath yarn and* wherein the composite core-sheath yarn comprises a core that is made from a monofilament yarn or a shape memory metal.

22. The textured fabric of claim 21, wherein the core is made from the shape memory material and wherein the shape memory material is an alloy of nickel and titanium.

23. The textured fabric of claim 21, wherein the core is the monofilament yarn and wherein the monofilament yarn is selected from the group consisting of: polyester, polyethylene, UHMWPE, polypropylene, PTFE, ePTFE, and nylon.

[24. The textured fabric of claim 21, wherein the sheath is made of a textured multifilament yarn.]

25. The textured fabric of claim [24] *13*, wherein the [sheath] *textured multifilament yarn* has a denier of from about 15 to about 40.

[26. The textured fabric of claim 24, wherein the sheath has a filament count of from about 5 to about 20.]

[27. The textured fabric of claim 24, wherein the sheath has a diameter of about 25 microns to about 250 microns.]

28. The textured fabric of claim 13, wherein the plurality of loops has a loop height of about 0.0250 inches to about [0.100 ] *0.110* inches.

29. The textured fabric of claim 13, [wherein the core-sheath yarn has a TPI of about 20 to about 40] *wherein the plurality of loops is formed from a composite core-sheath yarn*.

30. The textured fabric of claim [13] *29*, wherein the sheath is wrapped around a core, the sheath being provided externally of the core *and wherein the core-sheath yarn has a TPI of about 20 to about 40*.

31. A bioprosthetic heart valve comprising the textured fabric of claim 13.

32. A textured fabric for a bioprosthesis comprising:

a base layer *comprising yarns having a diameter from 20 microns to 80 microns*; and a plurality of loops projecting from the base layer, [,] *the plurality of loops comprising a textured multifilament yarn having a diameter from 10 microns to 250 microns and filament count from 5 filaments to 20 filaments;*

[wherein the plurality of loops is formed from a composite core-sheath yarn; and wherein the composite core-sheath yarn comprises a core and a sheath that is made from a different material from the core; and]

wherein the plurality of loops has a loop height of about 0.0250 inches to about [0.100 ] *0.110* inches[.] *and wherein the plurality of loops has a loop density from 900 loops/in$^2$ to 1,200 loops/in$^2$*.

33. The textured fabric of claim 32, wherein the base layer is a woven base layer comprising warp and weft yarns.

34. The textured fabric of claim [33] *32*, wherein the [warp and weft] *base layer comprises* yarns [are] made from a material [each] independently selected from the group consisting of: polyester, polyethylene, ultra-high molecular-weight polyethylene ("UHMWPE"), polypropylene, polytetrafluoroethylene ("PTFE"), expanded PTFE ("ePTFE"), and nylon.

35. The textured fabric of claim 33, wherein the warp and weft yarns are made of the same material.

36. The textured fabric of claim 33, wherein the warp and weft yarns are made of different materials.

[37. The textured fabric of claim 33, wherein the base layer comprises yarns having a diameter of about 20 microns to about 70 microns.]

38. The textured fabric of claim 33, wherein the base layer has an EPI of about 150 to about 300.

39. The textured fabric of claim 33, wherein the base layer has a PPI of about 100 to about 250.

40. The textured fabric of claim 32, *wherein the plurality of loops is formed from a composite core-sheath yarn comprising a core and a sheath that is made from a different material from the core, and* wherein the [composite core-sheath yarn comprises a] core [that] is made from a monofilament yarn or a shape memory metal.

41. The textured fabric of claim 40, wherein the core is made from the shape memory material and wherein the shape memory material is an alloy of nickel and titanium.

42. The textured fabric of claim 40, wherein the core is the monofilament yarn and wherein the monofilament yarn is selected from the group consisting of: polyester, polyethylene, UHMWPE, polypropylene, PTFE, ePTFE, and nylon.

[43. The textured fabric of claim 40, wherein the sheath is made of a textured multifilament yarn.]

44. The textured fabric of claim [40] *32*, wherein the [sheath] *textured multifilament yarn* has a denier of from about 15 to about 40.

[45. The textured fabric of claim 43, wherein the sheath has a filament count of from about 5 to about 20.]

[46. The textured fabric of claim 43, wherein the sheath has a diameter of about 25 microns to about 250 microns.]

[47. The textured fabric of claim 32, wherein the textured fabric has a loop density of about 400 loops/in$^2$ to about 1,000 loops/in$^2$.]

48. The textured fabric of claim 32, [wherein the core-sheath yarn has a TPI of about 20 to about 40 ] *wherein the plurality of loops is formed from a composite core-sheath yarn comprising a core and a sheath that is made from a different material from the core*.

49. The textured fabric of claim [32] *48*, wherein the sheath is wrapped around [a core] *the core*, the sheath being provided externally of the core, *and wherein the core-sheath yarn has a TPI of about 20 to about 40.*

50. A bioprosthetic heart valve comprising the textured fabric of claim 32.

51. A textured fabric for a bioprosthesis comprising:

a base layer *comprising yarns having a diameter from 20 microns to 80 microns*; and a plurality of loops projecting from the base layer[.] *the plurality of loops comprising a textured multifilament yarn having a diameter from 10 microns to 250 microns and a filament count from 5 filaments to 20 filaments;* wherein the plurality of loops is formed from a composite core-sheath yarn; [and wherein the composite core-sheath yarn comprises a core and a sheath that is made from a different material from the core; and]

wherein the core-sheath yarn has a TPI of about 20 to about 40 [.] *and*

*wherein the plurality of loops has a loop density from 900 loops/in$^2$ to 1,200 loops/in$^2$.*

52. The textured fabric of claim 51, wherein the base layer is a woven base layer comprising warp and weft yarns.

53. The textured fabric of claim [52] *51*, wherein the [warp and weft] *base layer comprises* yarns [are] made from a material [each] independently selected from the group consisting of: polyester, polyethylene, ultra-high molecular-weight polyethylene ("UHMWPE"), polypropylene, polytetrafluoroethylene ("PTFE"), expanded PTFE ("ePTFE"), and nylon.

54. The textured fabric of claim 52, wherein the warp and weft yarns are made of the same material.

55. The textured fabric of claim 52, wherein the warp and weft yarns are made of different materials.

[56. The textured fabric of claim 52, wherein the base layer comprises yarns having a diameter of about 20 microns to about 70 microns.]

57. The textured fabric of claim 52, wherein the base layer has an EPI of about 150 to about 300.

58. The textured fabric of claim 52, wherein the base layer has a PPI of about 100 to about 250.

59. The textured fabric of claim 51, *wherein the composite core-sheath yarn comprises a core and sheath that is made from a different material from the core and* wherein the [composite core-sheath yarn comprises a] core [that] is made from a monofilament yarn or a shape memory metal.

60. The textured fabric of claim 59, wherein the core is made from the shape memory material and wherein the shape memory material is an alloy of nickel and titanium.

61. The textured fabric of claim 59, wherein [the core is the monofilament yarn and wherein] the monofilament yarn is selected from the group consisting of: polyester, polyethylene, UHMWPE, polypropylene, PTFE, ePTFE, and nylon.

[62. The textured fabric of claim 59, wherein the sheath is made of a textured multifilament yarn.]

63. The textured fabric of claim [62] *51*, wherein the [sheath] *textured multifilament yarn* has a denier of from about 15 to about 40.

[64. The textured fabric of claim 62, wherein the sheath has a filament count of from about 5 to about 20.]

[65. The textured fabric of claim 62, wherein the sheath has a diameter of about 25 microns to about 250 microns.]

[66. The textured fabric of claim 51, wherein the textured fabric has a loop density of about 400 loops/into about 1,000 loops/in$^2$.]

67. The textured fabric of claim 51, wherein the plurality of loops has a loop height of about 0.0250 inches to about [0.100 ] *0.110* inches.

68. The textured fabric of claim 51, wherein the sheath is wrapped around a core, the sheath being provided externally of the core.

69. A bioprosthetic heart valve comprising the textured fabric of claim 51.

[70. A textured fabric for a bioprosthesis comprising:

a base layer; and a plurality of loops projecting from the base layer;

wherein the plurality of loops is formed from a composite core-sheath yarn; and wherein the base layer is a woven base layer comprising warp and weft yarns and wherein the base layer comprises yarns having a diameter of about 20 microns to about 70 microns;

wherein the composite core-sheath yarn comprises a core that is made from a monofilament yarn or a shape memory metal and a sheath that is made from a textured multifilament yarn;

wherein the sheath has a diameter of about 25 microns to about 250 microns; and wherein the plurality of loops has a loop height of about 0.0250 inches to about 0.100 inches.]

[71. A textured fabric for a bioprosthesis comprising:

a base layer; and a plurality of loops projecting from the base layer;

wherein the plurality of loops is formed from a composite core-sheath yarn; and wherein the base layer is a woven base layer comprising warp and weft yarns and wherein the base layer comprises yarns having a diameter of about 20 microns to about 70 microns;

wherein the composite core-sheath yarn comprises a core that is made from a monofilament yarn or a shape memory metal and a sheath that is made from a textured multifilament yarn;

wherein the sheath has a diameter of about 25 microns to about 250 microns; and wherein the core-sheath yarn has a TPI of about 20 to about 40.]

* * * * *